United States Patent
Baichwal et al.

(10) Patent No.: US 7,172,766 B2
(45) Date of Patent: *Feb. 6, 2007

(54) CONTROLLED RELEASE INSUFFLATION CARRIER FOR MEDICAMENTS

(75) Inventors: Anand Baichwal, Wappingers Falls, NY (US); John Staniforth, Bath (GB)

(73) Assignee: Penwest Pharmaceuticals Company, Danbury, CT (US)

( * ) Notice: Subject to any disclaimer, the term of this patent is extended or adjusted under 35 U.S.C. 154(b) by 1406 days.

This patent is subject to a terminal disclaimer.

(21) Appl. No.: 10/047,060

(22) Filed: Jan. 14, 2002

(65) Prior Publication Data

US 2002/0090345 A1 Jul. 11, 2002

Related U.S. Application Data

(60) Continuation of application No. 09/361,198, filed on Jul. 26, 1999, now Pat. No. 6,387,394, which is a continuation of application No. 08/787,762, filed on Jan. 28, 1997, now abandoned, which is a division of application No. 08/419,635, filed on Apr. 7, 1995, now Pat. No. 5,612,053.

(51) Int. Cl.
- *A61F 13/02* (2006.01)
- *A61K 9/50* (2006.01)
- *A61K 9/14* (2006.01)
- *A61L 9/04* (2006.01)

(52) U.S. Cl. ............... 424/434; 424/499; 424/500; 424/46

(58) Field of Classification Search ........... 424/440, 424/434, 499, 500, 400
See application file for complete search history.

(56) References Cited

U.S. PATENT DOCUMENTS

| | | |
|---|---|---|
| 2,587,215 A | 2/1952 | Priestly |
| 3,938,516 A | 2/1976 | Mathes |
| 3,964,483 A | 6/1976 | Mathes |
| 3,973,566 A | 8/1976 | Mathes |
| 4,013,075 A | 3/1977 | Cocozza |
| 4,200,099 A | 4/1980 | Guenzel et al. |
| 4,274,403 A | 6/1981 | Struve |
| 4,524,769 A | 6/1985 | Wetterlin |
| 4,590,206 A | 5/1986 | Forrester et al. |
| 4,741,872 A | 5/1988 | DeLuca et al. |
| 4,743,440 A | 5/1988 | Callingham et al. |
| 4,804,678 A | 2/1989 | Augstein et al. |
| 4,860,740 A | 8/1989 | Kirk et al. |
| 4,917,897 A | 4/1990 | Augstein et al. |
| 4,994,276 A | 2/1991 | Baichwal et al. |
| 5,042,472 A | 8/1991 | Bunin |
| 5,059,587 A | 10/1991 | Yamamoto et al. ............ 514/12 |
| 5,113,855 A | 5/1992 | Newhouse |
| 5,128,143 A | 7/1992 | Baichwal et al. |
| 5,135,757 A | 8/1992 | Baichwal et al. |
| 5,160,745 A | 11/1992 | DeLuca et al. |
| 5,176,132 A | 1/1993 | Drought et al. |
| 5,239,993 A * | 8/1993 | Evans et al. ............. 128/203.5 |
| 5,284,133 A * | 2/1994 | Burns et al. |
| 5,612,053 A * | 3/1997 | Baichwal et al. ........... 424/440 |
| 5,738,865 A | 4/1998 | Baichwal et al. |
| 6,387,394 B1 * | 5/2002 | Baichwal et al. ........... 424/440 |

FOREIGN PATENT DOCUMENTS

| | | |
|---|---|---|
| CA | 2115444 | 12/1993 |
| EP | 0079478 | 5/1982 |
| EP | 0371431 A2 | 6/1990 |
| EP | 0606486 A1 | 7/1994 |
| EP | 0611567 A1 | 8/1994 |
| GB | 2041763 | 9/1990 |
| WO | 9111179 | 8/1991 |
| WO | 9200771 | 1/1992 |
| WO | 9209322 | 6/1992 |
| WO | 9300076 | 1/1993 |
| WO | 9301157 | 5/1993 |
| WO | 9301158 | 5/1993 |
| WO | 9325193 | 12/1993 |
| WO | 9325198 | 12/1993 |
| WO | 9404133 | 3/1994 |
| WO | WO9422445 | 10/1994 |
| WO | WO9500127 A1 | 1/1995 |

OTHER PUBLICATIONS

Batra, et al., *J. Pharm. Sci.*, vol. 83(5):632-635 (May, 1994).
Suzuki, et al. *J. Microencapsulation*, vol. 11(2):197-203 (1994).
British Pharmacopoeia 1993 vol. II. Appendix XVII C A194-6.
3M Delivery vol. 4, Nov. 1994.
Abstract: Patent Abstracts of Japan, Publication No. 08198772 A, Aug. 6, 1996.

* cited by examiner

Primary Examiner—Carlos A. Azpuru
(74) Attorney, Agent, or Firm—Wilmer Cutler Pickering Hale & Dorr LLP

(57) ABSTRACT

Controlled release powder insufflation formulations are disclosed. The powder formulation includes cohesive composites of particles containing a medicament and a controlled release carrier which preferably includes one or more polysaccharide gums of natural origin.

18 Claims, No Drawings

CONTROLLED RELEASE INSUFFLATION CARRIER FOR MEDICAMENTS

This application is a continuation of U.S. patent application Ser. No. 09/361,198, filed on Jul. 26, 1999, now U.S. Pat. No. 6,387,394, which is a continuation of U.S. patent application Ser. No. 08/787,762, filed on Jan. 28, 1997, now abandoned which is a divisional of U.S. patent application Ser. No. 08/419,635, filed on Apr. 7, 1995, now U.S. Pat. No. 5,612,053.

BACKGROUND OF THE INVENTION

The advantages of controlled release products are well known in the pharmaceutical field and include the ability to maintain a desired blood level of a medicament over a comparatively longer period of time and increasing patient compliance by reducing the number of administrations necessary to achieve the same. These advantages have been attained by a wide variety of methods.

Many controlled release delivery systems have already been developed for absorption in the gastrointestinal tract and are commercially available. Likewise, controlled release transdermal formulations are well known in the art.

Another commonly utilized path for drug delivery is via oral inhalation therapy.

Inhalations are drugs or solutions or suspensions of one or more drugs capable of administration by the nasal or oral respiratory route for local or systemic effect. There are several different delivery devices which may be used to administer drugs to a patient via the inhalation route.

Nebulizers are suitable to administer inhalation solutions or suspensions only if they produce droplets sufficiently fine and uniform in size so that the mist reaches the bronchioles. Nebulized solutions may be breathed directly from the nebulizer or from a plastic face mask, tent, or intermittent positive breathing machine. Disadvantages of nebulized systems include "through-use" dose variability and drug stability problems.

Another group of products are known as inhalations or insufflations. The British Pharmacopoeia defines an inhalation as a liquid drug delivery system whereas an insufflation is a powder delivery system for the respiratory tract. One such inhalation device is the pressurized metered dose inhaler (PMDI). Devices of this type are intended for delivering metered doses of a drug to the respiratory tract and include suspensions or solutions in a liquefied gas propellant, along with materials such as co-solvents (e.g., alcohol) and surfactants (e.g. lecithin). A metered dose inhaler contains multiple doses, often in the range of one to two hundred doses. The dose delivered is generally in the range of 25 to 100 microliters (μl) per actuation.

Powdered drugs may be administered by mechanical devices that require externally-produced pressure or, more usually, deep inhalation by the patient. The powdered drug is often contained in a capsule which is placed in a suitable device and pierced to allow the powder to exit to the outside environment when an appropriate pressure drop is created. In certain devices, the pressure drop is created by having a patient place the device in his or her mouth and inhaling. Inhalation produces conditions which act to draw the drug out of the capsule and into the respiratory tract of the patient. The device may also contain turbulence-increasing structures which aim to enhance de-agglomeration, thereby preventing larger powder particles from entering the respiratory tract.

Increasing attention is now being given in the art to dry powder inhalers.

For example, International Patent Application WO 94/04133 describes a powder composition for inhalation which contains a microfine drug such as a salbutamol sulfate and a carrier containing an anti-static agent. The carrier is calcium carbonate or a sugar, especially lactose. The amount of carrier is 95–99.99 weight percent. The compositions were said to be useful for delivery of the active agent to the lungs while providing reduced side effects such as nausea by maximizing its proportion of drug reaching the lungs.

U.S. Pat. No. 4,590,206 describes capsules, cartridges or aerosol containers containing spray-dried sodium cromoglycate in finely divided and un-agglomerated form. A substantial proportion of the individual drug particles have shapes which allow deep penetration into the lung and yet are free-flowing so as to allow capsule filling.

International Patent Application WO 93/25198 is directed to an ultrafine powder for inhalation. The powder comprises a drug and hydroxypropyl cellulose and/or hydroxypropylmethyl cellulose. More than 80 weight percent of the particles in the powder are said to have a particle diameter of 0.5–10 microns. The powder is said to be able to reach the lower windpipe and bronchi and is further said to have good deposit (storage) properties, and is further said to be capable of releasing a drug continuously.

Previously, a hetero-disperse polysaccharide excipient system and controlled release oral solid dosage forms were described in our U.S. Pat. Nos. 4,994,276, 5,128,143, and 5,135,757, all of which are hereby incorporated by reference. These systems are commercially available under the tradename TIMERx™ from TIMERx Technologies, Patterson, N.Y. and Edward Mendell Co., Inc., N.Y., which is the assignee of the present invention.

It would be considered most advantageous in the art to provide new dry powder inhalation formulations which are capable of providing a slow, continuous release of drug while also being biodegradable or expellable from the pulmonary or nasal tract, and in which the active ingredient would be relatively bioavailable.

OBJECTS AND SUMMARY OF THE INVENTION

It is an object of the present invention to provide new oral or nasal inhalation carriers for a wide variety of medicaments which provide a reproducible in-vivo effect when a desired unit dose of the carrier in combination with a medicament is administered to a human patient via an oral or nasal inhalation device.

It is a further object of the present invention to provide a dry powder for oral or nasal inhalation or insufflation which comprises a cohesive composite of carrier and medicament, which provides a controlled release of medicament from the carrier in-vivo.

It is a further object of the present invention to provide a controlled release formulation for oral or nasal inhalation which is enzymatically degradable or expellable when administered in-vivo.

It is a further object of the present invention to provide a controlled release formulation for oral inhalation which enables controlled drug delivery in the naso-pharyngeal, tracheo-bronchial and combined naso-pharyngeal-bronchial regions of the pulmonary tract.

It is a further object of the present invention to provide a dry powder for inhalation therapy which is bioadhesive and which provides a controlled release of medicament when administered in-vivo.

It is a further object of the invention to provide an oral inhalation formulation for controlled release of a medicament in the upper airways of the respiratory tract.

The above-mentioned objects and others are achieved by virtue of the present invention, which relates in part to controlled release particles of a cohesive composite of a medicament together with a pharmaceutically acceptable carrier. The cohesive composite particles comprising the dry powder formulations of the invention are non-segregating. The average particle size is from about 0.1 to about 10 microns in diameter for lung delivery. For nasal delivery, the average particle size is from about 10 to about 355 microns and preferably 10–125 microns.

The pharmaceutically acceptable carrier can comprise, for example, xanthan gum, locust bean gum, galactose, other saccharides, oligosaccharides and/or polysaccharides, starch, starch fragments, dextrins, British gum and mixtures thereof. Preferably, the pharmaceutically acceptable carrier is of natural origin.

The pharmaceutically acceptable carrier can further comprise an inert saccharide diluent selected from a monosaccharide or disaccharide.

The present invention is further related to a capsule, cartridge or aerosol container containing a cohesive composite of a medicament together with a pharmaceutically acceptable polysaccharide carrier of natural origin, wherein the average particle size is from about 0.1 to about 10 microns in diameter for lung delivery. For nasal delivery, the average particle size is from about 1 to about 355 microns, and preferably from about 10 to about 125 microns.

The present invention is further directed to a method for preparing a controlled release pharmaceutical formulation for inhalation or insufflation therapy, comprising granulating a mixture of a medicament together with a polysaccharide gum of natural origin, drying the resultant granulation, and thereafter milling the resultant cohesive composite of medicament and gum to obtain particles having a diameter from about 2 to about 10 microns. In an alternative embodiment, the polysaccharide gum is first milled and (then granulated with the medicament, and the mixture is then dried to obtain a granulate, and the granulate is then screened to provide a dry powder product having a particle size from about 2 to about 10 microns in diameter.

In yet another embodiment, all of the saccharide component of the pharmaceutically acceptable carrier is dissolved or dispersed in a suitable medium. The medium selected should be capable of both suspending or dissolving the saccharide component as well as dissolving the actual ingredient. The active is added to the saccharide solution or dispersion and is dissolved or dispersed therein. The solvent is then removed, e.g., by evaporation, which may include spray drying, to produce a (poly)saccharide-active composite. The composite is then milled or screened, if necessary, to produce particles in the desired diameter.

The present invention is further directed to a method of treating a patient via oral or nasal inhalation therapy, comprising preparing the cohesive composite described above, incorporating the same into a suitable inhalation device, and administering a metered unit dose of the cohesive composite to a patient to provide a therapeutically effective dose of medicament for absorption in the upper respiratory tract or intra-nasally. The method preferably further comprises comminuting the controlled release carrier, or a granulate of controlled release carrier together with a medicament, such that the average particle size is from about 0.1 micron to about 10 microns in diameter. For purposes of the present invention, inhalation therapy shall be understood to include delivery of a medicament via oral-pharynx or nasal-pharynx routes.

In certain preferred embodiments of the invention, the controlled release carrier (comprising the gum of natural origin together with any pharmaceutically acceptable inert diluent) is included in an amount from about 99.9% to about 10%, and more preferably from about 99% to about 50%, by weight of the final product. The drug to gum ratio may be, e.g., from about 0.5:100 to about 1:1. More preferably, the drug to gum ratio is from about 1:100 to about 1:2. In embodiments of the invention where the controlled release carrier comprises both a gum of natural origin and a pharmaceutically acceptable inert diluent, the total amount of controlled release carrier is from about 10 to about 90% and the pharmaceutically acceptable inert diluent is from about 89 to about 9% of the formulation, the remainder comprising the medicament(s) to be administered.

For purposes of the present invention, the term "composite" shall be understood to encompass more than one particle of different chemicals, more than one particle of the same chemical or a single particle of more than one chemical. The term "chemical", shall be understood to include the active ingredient or medicament, carrier and inert diluent.

By "controlled release" it is meant for purposes of the present invention that the therapeutically active medicament is released from the formulation at a controlled rate such that therapeutically beneficial blood levels (but below toxic levels) of the medicament are maintained over an extended period of time, e.g., providing a dosage form which provides effective levels of the medicament in-vivo for a time period of from about 1 to about 24 hours or more.

The term "environmental fluid" is meant for purposes of the present invention to encompass, e.g., an aqueous solution, such as that used for in-vitro dissolution testing, or mucous found in the pulmonary or nasal tracts.

DETAILED DESCRIPTION

In general, it has been recognized in the art that dry powder inhalation or insufflation formulations must consist of particles of a size of about 2 microns in diameter in order for the particles, when inhaled, to reach the alveoli of the lungs. Particles larger than 10 microns in diameter are not able to reach the deep lung when inhaled because they are collected on the back of the throat and upper airways in humans, whereas those less than 0.5 microns tend to be re-breathed or exhaled). It is a surprising discovery of this invention, therefore, that when particles are formulated which exhibit bioadhesive release characteristics like those of the present invention, particles in the range of about 0.1 micron do not tend to be exhaled and are suitable for use in inhalation therapy.

In order to prepare particles having a size of 2 microns which are useful in an inhalation formulation, it is considered necessary to utilize a carrier material because particles of that small size tend to be cohesive, and further, the dose of pure drug is too small to allow for accurate dormitory for most drugs delivered by inhalation, thereby increasing the apparent size of the group of particles which have adhered to each other when inhaled. The separation of drug and carrier in the airway during the use of an oral inhalation device is generally due to different physical characteristics of the differently sized particles, frequently characterized by Stokes Number.

It has been found that the dry powder inhalation devices utilized in the prior art are not able to efficiently provide a dose of drug to the alveoli because they do not create enough turbulence. A high turbulence is needed to create shear conditions sufficient to isolate discrete drug particles of a size in the respirable fraction. Generally, one can expect that only 10–15% of the drug payload will be delivered into the deep lung areas for conventional devices, although this can be increased to 40–50% or more in newer devices. Further, due in part to the low efficiency of the delivery of drug to the deep lung areas, and partly due to prior art dry powder formulations themselves, many dry powder inhalation devices are considered to provide too variable a dose of medicament to be considered useful for many such medicaments.

In view of the above-mentioned problems and others, it is a goal of the present invention to provide a dose of drug which is absorbable in a controlled and efficient manner in the upper airways of the respiratory tract as well as in the deep lung areas of the respiratory tract. In these areas, generally referred to in the art as the tracheo-bronchial region, particles having a diameter of 0.1–10 microns will be able to be delivered to these areas. The amount of capillaries in the upper airways region of the respiratory tract is significantly less compared to the deep pulmonary region of the lungs, and therefore this region of the respiratory tract has not previously been targeted for drug delivery. In the present invention, the relatively fewer number of capillaries in the region is advantageously utilized to provide a slow, controlled release of drug from the cohesive composites of the dry powder formulations of the invention so as to get a longer controlled release and absorption of the medicament in comparison with the controlled release from an equivalent formulation penetrating the deep lung.

The invention relates in part to a dry powder inhalation/insufflation formulation which comprises a cohesive composite of a medicament together with a non-segregating carrier. In the aspects of the invention where the dry powder inhalation formulations of the invention are intended for lung delivery, at least 80% of the discrete polysaccharide/drug particles have an average particle size of from about 0.1 to about 10 microns. In other aspects where the drug/polysaccharide fine particles are carried on coarse saccharide particles, the composite particles will have an average particle size of from about 45 to about 355 microns, and preferably from about 63 to about 125 microns. In this manner, the cohesive composite particles, when inhaled via any dry powder inhalation device known in the art, will either be collected and absorbed mainly in the tracheobronchial region of the respiratory tract for 2–10 micron particles and in the deep lung for <2 micron particles. The carrier which is utilized to prepare the cohesive composite particles is one which will provide a controlled release of medicament when the particles are exposed to an environmental fluid, e.g., a dissolution liquid, mobile phase or water in an in-vitro dissolution apparatus, or, in the fluids present in the respiratory tract, and in particular, in the tracheobronchial regions in-vivo.

The carrier material utilized in the formulations of the present invention is preferably a naturally occurring gum. Such naturally occurring gums typically include the heteropolysaccharides and homopolysaccharides. The carrier, of course, can also include mixtures of homo- and heteropolysaccharides.

The term "heteropolysaccharide" as used in the present invention is defined as a water-soluble polysaccharide containing two or more kinds of sugar sub-units, the heteropolysaccharide having a branched or helical configuration, and having excellent water-wicking properties and immense thickening properties.

An especially preferred heteropolysaccharide is xanthan gum, which is a high molecular weight (approximately 1,000 kDa) heteropolysaccharide. Other preferred heteropolysaccharides include derivatives of xanthan gum, such as deacylated xanthan gum, the carboxymethyl ether, the propylene glycol ester and the polyethylene glycol esters.

The homopolysaccharides useful in the present invention include galactomannan gums, which are polysaccharides composed solely of mannose and galactose. Preferred galactomannan gums are those which are capable of cross-linking with the heteropolysaccharide. Galactomannans which have higher proportions of unsubstituted mannose regions have been found to achieve more interaction with the heteropolysaccharide when exposed to an environmental fluid. Locust bean gum, which has a higher ratio of mannose to the galactose, is especially preferred as compared to other galactomannans such as guar and hydroxypropyl guar.

Other naturally occurring polysaccharide gums known to those skilled in the food and pharmaceutical arts are also useful as the controlled release carrier of the invention. Such polysaccharides include alginic acid derivatives, carageenans, tragacanth, acacia, karaya, the polyethylene glycol esters of these gums, chitin, chitosan, mucopolysaccharides, konjac, starch, substituted starches, starch fragments, dextrins, British gums having a molecular weight of about 10,000 daltons, dextrans and the like. The starches can be in either native form, i.e., ungelled starches such as potato, corn, rice, banana, etc., or gelled starches or semi-synthetic starches.

Starch and starch fragments are especially preferred polysaccharides and the combination of xanthan gum with locust bean gum is an especially preferred gum combination. In our previous patents, we described and claimed the synergistic combination of heteropolysaccharide/homopolysaccharide gums for incorporation into solid oral dosage forms. Thus, in certain embodiments, the controlled release properties of the dry powder inhalation formulation are optimized when the ratio of heteropolysaccharide gum to galactomannan gum is from about 3:1 to about 1:3, and most preferably about 1:1. However, in this embodiment, the controlled release carrier of the invention may comprise from about 1% to about 99% by weight heteropolysaccharide gum and from about 99% to about 1% by weight homopolysaccharide gum.

If desired, a cationic cross-linking agent may be included in the dry powder formulations of the present invention. The cationic cross-linking agent may comprise, e.g., monovalent or multivalent metal cations. The preferred salts are the inorganic salts, including various alkali metal and/or alkaline earth metal sulfates, chlorides, berates, bromides, citrates, acetates, lactates, etc., providing the salts are soluble. Specific examples of suitable cationic cross-linking agents include calcium chloride, sodium chloride, potassium chloride, potassium sulfate, sodium carbonate, lithium chloride, tripotassium phosphate, sodium borate, potassium bromide, potassium fluoride, sodium bicarbonate, magnesium chloride, sodium citrate, sodium acetate, calcium lactate, and sodium fluoride. Multivalent metal cations may also be utilized. However, the preferred cationic cross-linking agents are monovalent or bivalent. Particularly preferred salts are potassium chloride and sodium chloride. The cationic cross-linking agent is included in the controlled release inhalation formulations of the present invention in an amount from about 0.1 to about 50% by weight, and more preferably from about 1% to about 10% by weight of the polysaccharide component.

In certain formulations of the invention, it may be desirable to add a pharmaceutically acceptable surfactant in a sufficient amount to either modify the release-controlling characteristics of the composite excipient/drug particles or the wetting and solubility characteristics of the drug. In such embodiments, the surfactant comprises from about 0.01 to about 10 percent of the controlled release carrier, by weight, and more preferably from about 0.1 to about 2 percent of the controlled release carrier, by weight. The surfactants which may be used in the present invention generally include pharmaceutically acceptable anionic surfactants, cationic surfactants, amphoteric (amphipathic/amphiphilic) surfactants, and non-ionic surfactants. Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, and alkyl sulfates.

Suitable pharmaceutically acceptable non-ionic surfactants such as, for example, polyoxyethylene compounds, lecithin, ethoxylated alcohols, ethoxylated esters, ethoxylated amides, polyoxypropylene compounds, propoxylated alcohols, ethoxylated/propoxylated block polymers, and propoxylated esters, alkanolamides, amine oxides, fatty acid esters of polyhydric alcohols, ethylene glycol esters, diethylene glycol esters, propylene glycol esters, glyceryl esters, polyglyceryl fatty acid esters, SPAN's (e.g., sorbitan esters), TWEEN's sucrose esters, and glucose (dextrose) esters. The surfactant should be non-sternutatory so as not to irritate the mucous membranes.

Other suitable pharmaceutically acceptable surfactants/co-solvents (solubilizing) agents include acacia, benzalkonium chloride, cholesterol, emulsifying wax, docusate sodium, glyceryl monostearate, lanolin alcohols, lecithin, poloxamer, poloxyethylene castor oil derivatives, poloxyethylene sorbitan fatty acid esters, poloxyethylene stearates, sodium lauryl sulfates, sorbitan esters, stearic acid, and triethanolamine.

Mixed surfactant/wetting agent systems are also useful in conjunction with the present invention. Examples of such mixed systems include, for example, sodium lauryl sulfate/polyethylene glycol (PEG) 6000 and sodium lauryl sulfate/PEG 6000/stearic acid.

The inert filler of the sustained release excipient preferably comprises a pharmaceutically acceptable saccharide, including a monosaccharide and/or a disaccharide. Examples of suitable inert pharmaceutical fillers include sugars such as sucrose, dextrose, lactose, galactose, fructose, mixtures thereof and the like as well as sugar alcohols such as mannitol, sorbitol, xylitol, lactitol, maltitol, galactitol and the like. However, it is preferred that a soluble pharmaceutical filler such as lactose, dextrose, galactose, sucrose, or mixtures thereof be used. In addition, it is to be understood that the above-mentioned sugars and sugar alcohols can also be used as carriers as well, in place of or in addition to the materials described above.

The properties and characteristics of a specific controlled release carrier or excipient system prepared according to the present invention is dependent in part on the individual characteristics of the homo- and heteropolysaccharide constituents, in terms of polymer solubility, glass transition temperatures etc. In certain embodiments which include both a hetero- and homopolysaccharide component with or without optional polysaccharide filler (e.g., lactose), the properties and characteristics of the resultant dry powder formulation will also be dependent in part on the synergism both between different homo- and heteropolysaccharides and between the homo- and heteropolysaccharides (severally or together) and the inert saccharide constituent(s) in modifying dissolution fluid-excipient interactions.

The dry powder insufflation/inhalation formulations are preferably prepared via a wet granulation method to obtain composite particles of medicament and carrier in the desired respirable size range (depending on whether designed for naso-pharyngeal depositions, shallow lung or deep lung deposition, or some combination thereof). In certain embodiments, such composites are provided via the use of one or more wet granulation steps. However, the dry powder formulations of the invention may be prepared according to any technique to yield an acceptable product.

In one aspect of the invention, the dry powder insufflation formulations are prepared as follows:

a drug is dissolved in a suitable solvent (e.g., water, alcohol, mixed solvents, etc.) and added to a polysaccharide or polysaccharide mixture in the desired size range. For oral insufflations, this will be 80% less than 10 microns; for nasal insufflations, the desired size range will be about 10 to about 355 microns. Where required, the polysaccharides can be sieved to obtain the required size. In cases where the polysaccharide requires size reduction, a suitable milling method may be used, such as fluid energy milling (e.g., with micronizers or jet mills); hammer milling, vibrational milling, ball milling, etc. In some cases, it will be more beneficial to carry out the milling procedure below the glass transition temperature or for other reasons, to use cryogenic milling (using liquid $CO_2$, $N_2$, or other suitable cooling aid).

The concentration (or volume) of drug solution added to such fine polysaccharide particles will be an amount sufficient to provide enough wetting contact to create sufficient drug absorption into the polysaccharide surface and absorption onto the surface (this is especially important for starch) so as to yield the controlled release characteristics required. This will typically require an aqueous concentration of 10–50% w/w of polysaccharides. The absolute concentration being dependent on other method factors including time of wetted contact of solution with polysaccharide surfaces and/or temperatures during or preceding wetted contact. This latter parameter is particularly important in the case of polysaccharides which require elevated temperatures to undergo solubility/gel transformations in certain circumstances (e.g., start to starch mucilage or locust bean gum sol to gel transformation). The contact time is preferably in the range of about 1 to 30 minutes in a high speed mixer, processor or other granulating means. The elevated temperature will be 80° to 100° C. for starch and locust bean gum, although this is preferably not the temperature following contact with drug solution.

The contacted drug-polysaccharide wet mass can then be granulated in the usual way using either a high speed mixture granulator or spray granulated to provide liquid contact or other suitable method to provide composite particles in the entrainable size range (for delivery from an insufflator) usually 45–355 microns (and preferably 63–95 microns for non-compression insufflation). The powder or granular material is then dried, for example, using a tray drier or fluidized bed drier operated at approximately 60° C. for a sufficient time to produce equilibrium moisture content conditions in the powder/granules. In the case of some drugs/bioactives using a freeze drying method so as to avoid physical/chemical degradation. Finally, for some presentations (inhaler types or clinical uses), it may be desirable to apply a final further size reduction to the dried powder/granules. This can be carried out using one of the methods described above or by sieving.

In another aspect of the invention, a second method for preparing the insufflation formulations of the present invention is provided. The method described above is followed except that the volume of liquid used is much higher (e.g., 50–99% w/w water to polysaccharides) so as to provide a more complete gelation/solubilization of the polysaccharide components before or during contact with the drug solution. In such cases, the drying method may be by one of the methods described in the procedure described above or by spray drying or drum drying or spin flash drying, moving film drying or other suitable method. Alternatively, a dewatering step can be introduced prior to drying, e.g., using osmotic effects across a semi-permeable membrane. If necessary, final dried drug-loaded gel matrix can then be milled to provide powder in the desired size range using one of the methods described above.

A still further aspect of the invention provides a third method for preparing the formulations of the present invention. The first method is repeated except that the drug is milled or spray dried to the respirable range (0.1 to 10 microns for pulmonary use, or higher for nasal use) and applied as a suspension to the polysaccharide system in a largely solid/semi-solid state (first method) or semi-solid/liquid state (second method). The drug suspension can either be sprayed onto the polysaccharide powder (spray granulation) or be added in a high speed mixer granulator or other granulating means.

A fourth method for preparing the formulations of the present invention includes preparing a simple dry blend of fine drug particles (0.1–10 microns) with fine polysaccharide particles (0.1–10 microns) using a suitable dry blender (e.g., Turbula™ mixer).

A fifth method for preparing the formulations of the present invention includes following the fourth procedure but adding water or other suitable solvent(s) to provide a composite of the blended drug/polysaccharides. Drying and screening size reduction, if required, can be carried out as described above.

Yet another (sixth) method for preparing the formulations of the present invention includes incorporating a saccharide component with the drug and polysaccharide blend. This method includes dissolving all the saccharide component along with the drug and adding it in a manner described any of the first three methods. Alternatively, the saccharide component may be added in solutions in the solvent system as described in the fifth method. The saccharide component can also be milled to the respirable fraction (0.1–10 microns for pulmonary, 10–355 microns for nasal) and dry blended with the products prepared by any of the five foregoing methods. Alternatively, the saccharide component may be fractionated to a size range suitable for functioning as a carrier capable of enhancing powder entrainment and deaggolomeration during inspiration from a dry powder insufflator. For this purpose, the saccharide component should be in the size range 45–355 microns and preferably 63–125 microns. The composite controlled release material prepared in any of the foregoing five methods is dry blended for 5–30 minutes with the saccharide using a tumbling blender,(e.g., Turbula mixer).

A seventh method of preparing the formulations of the present invention involves cases where it may be desirable to add a further inert component, such as a surf actant, lubricant, etc. This may be done by suitable addition into any of the foregoing methods. In the first, second, third and fifth methods, the addition is made in the liquid state. In the fourth and sixth methods, the additive is in the solid state and added by simple dry blending.

A wide variety of medicaments can be utilized in the dry powder inhalation/insufflation formulations of the present invention. In general, medicaments which may be used in conjunction with the invention are preferably locally acting on the pulmonary tissue and/or be absorbable from the respiratory tract in sufficient quantities to provide a therapeutically desired effect.

Such medicaments include the following:

(a) anticholinergic agents such as anisotropine, atropine, belladonna alkaloids, benztropine, biperiden, dicyclomine, glycopyrrolate, hyoscyamine, ipratropium, isopropamide, mepenzolate, methscopolamine, oxyphencyclimine, procyclidine, propantheline, scopolamine, tridihexethyl, trihexyphenidyl and cyclopentolate;

(b) corticosteroids such as beclomethasone, betamethasone, dexamethasone, hydrocortisone, methylprednisolone, prednisolone, clocortolone, flumethasone, fluocinolone, fluorometholone, flurandrenolide, triamcinolqne, budesonide, desoximetasone, halcinonide, amcinonide, clobetasol, diflorasone and fluocinonide, fluticasone;

(c) sympathomimetics such as albuterol, albuterol sulfate, dobutamine hydrochloride, dopamine hydrochloride, ephedrine sulfate, epinephrine, fenfluramine hydrochloride, isoetharine, isoproterenol, mephentermine sulfate, metaproterenol sulfate, metaraminol bitartrate, methoxamine hydrochloride, norepinephrine bitartrate, phenylephrine hydrochloride, phenylpropanolamine hydrochloride, pseudoephedtine, ritodrine hydrochloride, terbutaline sulfate, tetrahydrozoline hydrochloride, triprolidine and pseudoephedrine, and xylometazoline hydrochloride;

(d) posterior pituitary hormones such as nafarelin acetate and vasopressin;

(e) anti-hyperglycemic agents such as acetohexamide, chloropropamide, glipizide, glyburide, insulin preparations, tolazamide and tolbutamide;

(f) decongestants such as pseudoephedrine, phenylpropanolamine hydrochloride;

(g) bronchodilators such as albuterol, albuterol sulfate, atropine sulfate, bitolterol mesylate, dyphylline, epinephrine, ethylnorepinephrine hydrochloride, ipratropium bromide, isoetharine, isoproterenol, metaproterenol sulfate, oxtriphylline, pirbuterol acetate, terbutaline sulfate and theophylline/aminophylline, salmeterol (and salts);

(h) $beta_2$-adrenergic agonists such as albuterol, bitolterol mesylate, metaproterenol sulfate, pirbuterol acetate, ritodrine hydrochloride and terbutaline sulfate;

(i) antihistamines such as astemizole, azatadine maleate, brompheniramine maleate, buclizine hydrochloride, carbinoxamine, pseudoephedrine, chlorpheniramine maleate, clemastine fumarate, cyclizine, cyproheptadine hydrochloride, dexchlorpheniramine maleate, dimenhydrinate, diphenhydramine hydrochloride, hydroxyzine, meclizine hydrochloride, methdilazine hydrochloride, promethazine hydrochloride, propiomazine hydrochloride, terfenadine, trimeprazine tartrate, tripelennamine, triprolidine, cromones such as cromolyn sodium, and nedocromil (and salts).

(j) cytolcines, cytokine inhibitors (e.g., leucovorin), polypeptides, peptides, polypeptides, proteins, e.g., heparin, enzymes, genes, gene fragments, hormones, and N-acetylcysteine.

The above list of drug classes and particular medicaments is by way of example only and is not meant to be exclusive.

Insufflation Inhalation Devices

In general, insufflation inhalation devices suitable for use in connection with the inventive controlled release particulate dosage forms comprise a housing having a passageway for the flow of air, in which one end of the passageway is designed for insertion in the mouth or nose, a chamber containing controlled release particles of a cohesive composite of a medicament together with a pharmaceutically acceptable polysaccharide carrier suitable for oral inhalation, wherein the average discrete particle size is from about 0.1 to about 10 microns in diameter for the or-pulmonary route or 10 to 355 microns for the nasal route, actuating means for releasing a unit dose of the particles into said passageway, such that the unit dose is drawn through said passageway during an inspiration by the patient and is delivered to the naso-pharynx and/or the pulmonary tract of the patient.

The formulations of the present invention may be adapted for use with respect to any oral and/or nasal insufflation device for powdered or solid medicaments. For example, the composite powder of the present invention may be compressed into a solid dosage form such as a ring tablet which is then placed into an appropriate insufflation device which includes comminuting or other means for providing discrete powder particles in the respirable fraction from the insufflation device when the device is actuated (e.g., when a unit dose of medicament is to administered via inspiration).

There are many devices described in the prior art which are useful for delivering a dose of powdered drug to the respiratory tract or naso-pharynx of a patient. Examples of such devices which would be useful in delivering the formulations of the present invention are described below.

One such device is known as the Bespak device described in PCT publication WO 92/00771, hereby incorporated by reference, and available from Innovata Biomed Limited. The device described therein includes a storage chamber for storing a powdered drug to be administered and a metering member having metering cups in which individual doses of the powdered drug are placed. Air is inhaled through an inhalation passage at one end of the device and directed into contact with the metering cup that has been filled with the powdered drug. The metering cup is oriented upwardly open to face the air stream and to enable the powder to be released from the cup. Upon inhalation, the dose is mixed with the air flow and continues through the mouthpiece to be inhaled.

The metering cups on the metering member are arranged on an outer frusto-conical wall so that each metering cup is positionable to be upwardly open and face the air flow during inhalation. The metering member rotates so that the metering cups move between a position in which the cup receives a dose of the powered drug from the storage chamber to a position in which the cup is exposed to the air flow. As one cup is exposed to the air flow, another cup is aligned with the storage chamber and is being filled with powder.

After the dose is blown from the metering cup, and upon subsequent rotation of the metering member, the cup is wiped and cleaned by a wiping element to remove any un-dispersed powder and then dried via a moisture absorbent material.

Another device for delivery of inhalation powders is described in U.S. Pat. No. 2,587,215 (Priestly), hereby incorporated by reference. Priestly describes an inhaler having a storage chamber containing a powdered medicament, a mixing chamber and means to move a set dose of medicament from the storage chamber to the mixing chamber. The dose is mixed with air in the mixing chamber and inhaled through a mouthpiece.

Yet another inhalation device suitable for delivering powdered inhalation drugs is described in U.S. Pat. No. 4,274,403 (Struve), hereby incorporated by reference. Struve describes an inhaler for administering a powdered drug nasally, which includes storage means for containing a quantity of the drug therein. The storage means includes a feed hole through which the powdered drug may be received from the storage means. The device further includes a dispensing head operatively coupled to the storage means for dispensing the powdered drug more nasally. The dispensing head of the Struve inhaler includes a nozzle, a body portion, a dispensing cylinder and a vent means. The nozzle is shaped to be received in the nasal passage of the user. The nozzle includes a dispensing passageway for dispensing the dose into the nasal cavity of patient.

The body portion is located adjacent the nozzle and has a traverse bore therein. The traverse bore operatively connects the dispensing passageway in the nozzle with the feed hole leading to the drug storage means. The feed hole and the dispensing passageway are transversely offset relative to one another at the points where they enter the transverse bore.

The dispensing cylinder includes a metering chamber. The metering chamber may be selectively aligned with either the feed hole or the dispensing passageway. The dispensing cylinder is slidably received in the transverse bore for movement between a first transverse position in which the metering chamber is aligned with the feed hole and a second transverse position in which the metering chamber is aligned with the dispensing passageway. In its first position, the metering chamber can be filled with a charge of the powdered drug when the inhaler is manipulated. In the second position, places the charge of the powdered drug into the dispensing passageway for inhalation by the user.

The vent means is formed as part of the dispensing cylinder and is capable of venting the metering chamber to atmosphere only in the second position of the cylinder, i.e. when the powder disposed in the device such that it may be inhaled by the user.

Another inhaler device is disclosed in U.S. Pat. No. 4,524,769 (Wetterlin), hereby incorporated by reference. Wetterlin describes a dosage inhaler for administering a micronized pharmacologically active substance to a patient. The inhaler includes a gas conduit means through which gas passes for carrying the micronized substance to be administered. The inhaler further includes a membrane having a plurality of preselected perforated portions, each portion adapted to hold and dispense a reproducible unit dose of less than 50 mg of said active substance, in dry powder form. The powder particles have a particle size of less than 5 micrometers. The membrane is movably connected to the gas conduit means so that one of the preselected portions can be positioned within the gas conduit means so that the substance held in the preselected portion may be dispensed. The remaining preselected portion can be in a position external to said gas conduit means to receive said active substance. The membrane is movable through a plurality of positions whereby each preselected portion of the membrane can be successively positioned within the gas conduit to dispense the unit dose of the active substance held therein. Each preselected portion from which the active substance has been dispensed can be moved to said external position to receive active substance.

GB Patent Application No. 2,041,763, hereby incorporated by reference, describes an inhaler having a powder storage chamber and a rotatable metering member having dosing holes which open to the storage chamber in one position and open to the mixing chamber in another position. Upon rotation of the metering member, the powder is carried from the storage chamber to the mixing chamber to be inhaled.

EP 0 079 478, hereby incorporated by reference, describes an inhaler having a storage chamber, inhalation air passage and rotatable delivery member having a cavity formed therein. The delivery member is rotated from one position in which the cavity receives powder from the storage chamber to another position in which the powder falls from the cavity by the effect of gravity into a collector positioned in the air passage.

U.S. Pat. No. 4,860,740 (Kirk et al.), hereby incorporated by reference, describes an inhaler having a rotatable metering member with recesses formed therein. The recesses contain a powdered medicament. Upon rotation of the metering member, one of the recesses in exposed to the air inhalation passage to be entrained in the air stream and inhaled.

The Easyhaler™, described in PCT publication WO 92/09322, hereby incorporated by reference, and available from Boehringer Ingelheim is illustrative of another suitable device for delivering the formulations of the present invention. The device includes a supply of a pulverized medical substance and a "dosing means", which is a rotatable cylinder having five uniform recesses arranged around the periphery of the cylinder. The cylinder is rotated such, hat one recess aligns with the supply of drug and is filled by a quantity of the drug while another recess aligns with an air channel connected to the mouthpiece. The filled recess is then rotated to another position in the direct path of an inhalation air flow. The dose is pre-set by the recessed portion of the rotatable dosing means and is flushed clean by the direct air flow through the inhalation chamber.

To operate the device, the rotating dosing means is turned so that a full dosing chamber (having already been filled up after the previous use) is rotated into alignment with the air channel leading to the mouthpiece. Upon inhalation by the user, air is drawn through apertures and nozzles directly into the dosing chamber. The air flow flushes the dosing chamber causing the drug to be carried with the air in the direction of the inhalation through the mouthpiece. The axis of the air channel is arranged at an angle to the axis of the dosing means of between 70° and 110°, but preferably 90° (perpendicular).

U.S. Pat. No. 5,176,132, hereby incorporated by reference, discloses a device for the administration to the lung by inhalation of a medicament in powdered form. The device includes a mouthpiece, a medicament reservoir communicating with said mouthpiece, and metering means for dispensing a dose of medicament from the reservoir. The reservoir contains a compacted body of powdered medicament including an active ingredient having a particle size of from 1 to 10 µm when in loose powder form. The metering means includes a rotatable helical blade for abrading the compacted body. Thus when actuated, the helical blade abrades the compacted powdered medicament into particles capable of being inhaled into the respiratory tract of a patient.

International patent applications, PCT/EP93/01157 and PCT/EP93/01158 (assigned to GGU), hereby incorporated by reference, are directed to an inhalation device and to a annular tablet, respectively. GGU's device includes a medicament reservoir body situated in a mouthpiece. The body forms the beginning of an inhalation tube through which the medicament is inhaled. The drug is in a compacted and annular (ring) form. In use, a face mill cutter rotates, generating particles of the drug. Upon inhalation, air flows through air inlet openings in the casing and in the area of the cutting edges of the face mill cutter. Together with depressions situated between the cutting edges, the inlet openings and the depressions form an air channel leading to the mouthpiece, through which the drug particles are inhaled.

The quantity of each dose is determined by the amount of rotations of the face mill cutter. A spring presses the inhalation tube and thus the drug body toward the face mill cutter. In operation, a wind-up button is rotated to load the spring. By pressing the trigger mechanism, the spring is released thereby rotating the upper portion to which is connected the face mill cutter.

According to PCT/EP93/01158, the supply of pharmaceutical agent is present in solid, tablet form and has an isotropic solid structure. The strength, density and composition of the solid is homogenous. The tablets are made via cold isostatic compression at pressures between 50–500 megapascals (MPa).

Compressed Formulations

The cohesive composite particles comprising the dry powder insufflation formulations of the invention are capable of being compressed into a solid mass for insertion into a suitable inhalation device. In the event that the formulation is to be compressed, an effective amount of any generally accepted pharmaceutical lubricant, such, as HVO or PEG, may be added to the above-mentioned ingredients of the excipient at the time the medicament is added, or any time prior to compression into a solid dosage form. Suitable lubricants can be added in an amount of from about 0.5% to about 3% by weight of the solid dosage form. An especially preferred lubricant is sodium stearyl fumarate, NF, commercially available under the trade name Pruv® from the Edward Mendell Co., Inc.

DETAILED DESCRIPTION OF THE PREFERRED EMBODIMENTS

The following examples illustrate various aspects of the present invention. They are not to be construed to limit the claims in any manner whatsoever.

EXAMPLE 1

30.0522 grams of dry xanthan gum is blended with 30.0284 grams of locust bean gum in a food processor on the high speed setting for about 15 seconds. 7.5516 grams of a solution containing 16.0165 grams of albuterol sulfate in 200.05 grams of ethanol is added to the blended gums in the food processor and blended on the high speed setting for 1 minute to form a wet composite.

The wet composite is screened through a 355 micron sieve and then dried at 60° C. to approximately equilibrium moisture content (about 4 percent LOD). The dried composite is then screened through 45, 63 and 125 micron sieves. The greater than 45 micron, 45–63 micron, and the 63–125 micron fractions are separately packed and sealed in bottles containing desiccant cartridges to preserve the bioactive characteristics of the gums and avoid swelling of the gums prior to inhalation.

EXAMPLE 2

The procedure set forth in Example 1 is repeated except that the following ingredients are used:
- 30.0624 grams of xanthan gum
- 30.0520 grams of locust bean gum
- 3.7585 grams of a solution containing 24.073 grams of albuterol sulfate in 300.05 grams of water The resulting dried composite is screened in the same manner and the fractions obtained were separately packaged in sealed containers containing desiccant cartridges.

EXAMPLE 3

In this example, 40.0024 grams of lactose and 5.0217 grams of a solution containing 16.0165 grams of albuterol sulfate in 200.05 grams of ethanol are added to a food processor, and blended for 1 minute. The resultant wet granulate is screened through a 355 micron sieve. The screened composite is then dried at 60° C. to about 4 percent LOD. The dried composite is then screened through 45, 63, and 125 micron sieves. The less than 45 micron, 45–63 micron, and 63–125 micron fractions are separately packed in sealed bottles containing a desiccant cartridge.

EXAMPLE 4

In-vitro Drug Delivery Studies

In this example, the products of Examples 1–3 were studied to determine drug delivery of the respective formulations. The fraction containing 45–63 micron particles for each of the products prepared in Examples 1–3 were placed into size 3 gelatin capsules (20 mg±2 mg). The 45–63 micron fraction was selected to insure shallow lung penetration. The studies were conducted using a Twin Stage Impinger (TSI) apparatus A as described in *British Pharmacopeia*, 1993, Vol. II (Appendix XVII C, page A 194), incorporated by reference herein. The TSI and monograph provide a determination of the deposition of a dose emitted from a pressurized inhaler. According to the monograph, the upper and lower impingement chambers correspond to shallow lung and deep lung regions. Thus, by measuring the amount of active ingredient recovered from each chamber, the artisan can determine the amount of drug delivered to each area which is measured as a percentage of the total dose.

Following the procedures set forth in the *British Pharmacopeia*, supra, separate TSI analyses were carried out for each product, i.e., Examples 1, 2 and 3. A filled capsule was fitted individually into a MIAT cyclohaler containing specially molded mouthpiece to fit the inlet to the TSI. The capsules were pierced in the cyclohaler. At each time period indicated in the tables below, the TSI was activated for 10 seconds at 60 dm$^3$/minute. The device was then disassembled and the liquid in Stages 1 and 2 of the TSI was analyzed by spectrofluorimetry to determine the amount of drug delivered, (excitation wavelength: 235 nm; emission wavelength: 303 nm; scan speed: fast; excitation slit width: 10 nm; sensitivity: low; emission slit width: 10 nm; excitation start wavelength: 200 nm; emission start wavelength: 250 nm; emission end wavelength: 350 nm; excitation end wavelength: 300 nm).

Disassembling of the TSI and analysis was carried out at the different times shown in the Tables below after firing in order to determine the quantities of drug released into stage 1 and stage 2 liquid at the times shown. The results obtained for each of the formulations of Examples 1–3 is provided below:

RESULTS

MEAN DRUG CONCENTRATION (µg)

| Time (Minutes) | STAGE 1 Amount | % | STAGE 2 Amount | % |
|---|---|---|---|---|
| EXAMPLE 1 ALBUTEROL RELEASED (µg) FROM 112 µg TOTAL CONTENT (9% R.S.D.) | | | | |
| 0 | 0 | 0 | 0 | 0 |
| 15 | 5.55 | 4.96 | 1.31 | 1.17 |
| 30 | 3.99 | 3.56 | 0.74 | 0.66 |
| 45 | 4.86 | 4.34 | 0.87 | 0.78 |
| 60 | 4.70 | 4.20 | 1.11 | 0.99 |
| 240 | 11.8 | 10.54 | 5.2 | 4.64 |
| 360 | 15.0 | 13.39 | 10.2 | 9.11 |
| EXAMPLE 2 ALBUTEROL RELEASED (µg) FROM 26.7 µg TOTAL CONTENT (10% R.S.D.) | | | | |
| 0 | 0.18 | 0.67 | 0.5 | 1.81 |
| 15 | 1.97 | 7.38 | 0.13 | 0.49 |
| 30 | 3.93 | 14.72 | 0.53 | 1.99 |
| 45 | 4.73 | 17.72 | 0.57 | 2.13 |
| 60 | 4.97 | 18.61 | 0.59 | 2.21 |
| 120 | 6.9 | 25.84 | 1.1 | 4.12 |
| EXAMPLE 3 ALBUTEROL RELEASED (µg) FROM 153.8 µg TOTAL CONTENT (2% R.S.D.) | | | | |
| 0 | 30.08 | 19.56 | 0.32 | 0.21 |
| 15 | 29.46 | 19.15 | 0.88 | 0.57 |
| 30 | 25.34 | 16.48 | 0.37 | 0.24 |
| 45 | 27.76 | 18.05 | 0.1 | 0.07 |
| 60 | 30.88 | 20.08 | 0.45 | 0.29 |

From the foregoing data, it can be seen that the products of examples 1 and 2 where the drug is associated with a polysaccharide, the amount of drug released at time=0 into both chambers is zero or close to zero and increases over the release periods studied in a controlled manner. In the case of the product of example 3, in which the drug is only associated with lactose, the total payload of drug available for release is released at time=0 with no significant further drug release after that time period. Therefore, the drug concentration, drug:polysaccharide ratio, and manner of drug loading on the carrier are significant controlling or influencing drug release from the insufflation formulations of the present invention.

The examples provided above are not meant to be exclusive. Many other variations of the present invention would be obvious to those skilled in the art, and are contemplated to be within the scope of the appended claims.

What is claimed is:

1. A device for delivering a medicament to a patient, comprising
    an output port defining a passage for dispensing controlled release particles of a cohesive composite of a medicament and a pharmaceutically acceptable carrier to a patient;
    a chamber containing the cohesive composite particles of the medicament and the pharmaceutically acceptable carrier, the pharmaceutically acceptable carrier comprising xanthan gum and locust bean gum, wherein the average particle size of said cohesive composite particles is from about 0.1 to about 125 microns in diameter; and an actuator coupled to the chamber, the actuator selectively causing the cohesive composite particles to be dispensed to the patient through the passage of the output port.

2. The device of claim 1, wherein said pharmaceutically acceptable carrier comprises said xanthan gum and said locust bean gum in a ratio of from about 1:3 to about 3:1.

3. The device of claim 1, wherein the average particle size of said cohesive composite particle is from about 0.1 to about 10 microns.

4. The device of claim 1, wherein the average particle size of said cohesive composite particle is from about 10 to about 125 microns.

5. The device of claim 1, wherein the medicament to gum ratio is from about 0.5:100 to about 1:1.

6. The device of claim 5, wherein the medicament to gum ratio is from about 1:100 to about 1:2.

7. The device of claim 1, further comprising from about 0.1 to about 50% by weight of a cationic cross-linking agent comprising an alkaline metal or an alkaline earth metal sulfate, chloride, borate, bromide, citrate, acetate or lactate.

8. The device of claim 7, wherein said cationic cross-linking agent is present in an amount of from about 1 to about 10% by weight.

9. The device of claim 7, wherein said cationic cross-linking agent is selected from the group consisting of potassium chloride and sodium chloride.

10. The device of claim 1, wherein said pharmaceutically acceptable carrier further comprises an inert saccharide diluent selected from the group consisting of monosaccharides, disaccharides and mixtures thereof.

11. The device of claim 10, wherein said inert saccharide diluent is selected from the group consisting of dextrose, sucrose, galactose, lactose and mixtures thereof.

12. The device of claim 1, wherein said pharmaceutically acceptable carrier further comprises a pharmaceutically-acceptable surfactant in an amount of from about 0.5 to about 3% by weight of the controlled release carrier.

13. The device of claim 12, wherein said surfactant is selected from the group consisting of pharmaceutically-acceptable anionic surfactants, cationic surfactants, amphoteric (amphipathic/amphophilic) surfactants, non-ionic surfactants, and mixtures thereof.

14. The device of claim 1, wherein said controlled release particles are compressed together to form a solid mass.

15. The device of claim 1, wherein said controlled release pharmaceutical is suitable for delivery to the upper respiratory tract of a human patient.

16. The device of claim 1, wherein said controlled release pharmaceutical is suitable for oral insufflation therapy.

17. The device of claim 1, wherein said cohesive composite is in the form of a granulate.

18. A device for delivering a medicament to a patient, comprising a cohesive composite of a medicament together with a pharmaceutically acceptable carrier comprising xanthan gum and locust bean gum, wherein the average particle size of said cohesive composite particles is from about 0.1 to about 125 microns in diameter; and means for delivering the cohesive composite to a nasal or oral orifice.

* * * * *